United States Patent [19]

Brox et al.

[11] Patent Number: 4,829,057
[45] Date of Patent: May 9, 1989

[54] OXYTETRACYCLINE CAPSULES WITH INCREASED STABILITY AND METHODS OF PRODUCING THE SAME

[75] Inventors: Werner Brox, Beerfelden, Fed. Rep. of Germany; Artur Burger, Innsbruck, Austria

[73] Assignee: R. P. Scherer Corporation, Troy, Mich.

[21] Appl. No.: 196,762

[22] Filed: May 13, 1988

Related U.S. Application Data

[63] Continuation of Ser. No. 757,001, Jul. 19, 1985, abandoned.

[30] Foreign Application Priority Data

Jul. 24, 1984 [DE] Fed. Rep. of Germany ....... 3427238

[51] Int. Cl.$^4$ .......................... A61K 9/48; A61K 9/66; A61K 31/65
[52] U.S. Cl. .................................. 514/152; 53/266 R; 264/4.1; 424/451; 424/452; 424/455; 424/456; 514/962
[58] Field of Search ............. 53/266 R; 424/451, 452, 424/455, 456; 514/152

[56] References Cited

U.S. PATENT DOCUMENTS

| | | |
|---|---|---|
| 2,234,479 | 3/1941 | Scherer .................................. 424/37 |
| 2,298,122 | 10/1942 | Hailer et al. .......................... 424/37 |
| 2,585,903 | 2/1952 | Meyer .................................... 424/37 |
| 2,867,661 | 1/1959 | Buckley, Jr. et al. ............... 260/559 |
| 2,870,062 | 1/1959 | Stanley et al. ......................... 424/37 |
| 2,915,555 | 12/1959 | Solomons, III ..................... 260/559 |
| 3,655,864 | 4/1972 | Grass et al. ............................ 424/38 |
| 3,696,189 | 10/1972 | Snyder ................................... 424/38 |
| 3,867,521 | 2/1975 | Miskel et al. .......................... 424/37 |
| 3,960,757 | 6/1976 | Morishita et al. ..................... 424/38 |
| 4,080,445 | 3/1978 | Lin et al. .............................. 514/152 |
| 4,102,806 | 7/1978 | Kondo et al. .......................... 424/38 |
| 4,610,868 | 9/1986 | Fountain et al. ...................... 424/31 |

FOREIGN PATENT DOCUMENTS

| 2631281 | 1/1978 | Fed. Rep. of Germany ........ 424/37 |
| 2631282 | 1/1978 | Fed. Rep. of Germany ........ 424/37 |

OTHER PUBLICATIONS

Wm. Ebert "Soft Elastic Gelatin Capsules: A Unique Dosage Form" 8 page reprint from Pharmaceutical Technology Oct. 1977.
Chemical Abstracts 73:38500h (1970), Baluteov.
Chemical Abstracts 98:22189u (1983), Graskovskays.

*Primary Examiner*—Shep K. Rose
*Attorney, Agent, or Firm*—Allegretti & Witcoff, Ltd.

[57] ABSTRACT

Soft elastic gelatin capsules containing primarily the crystalline form A of oxytetracycline hydrochloride exhibit increased storage ability.

6 Claims, 4 Drawing Sheets

OXYTETRACYCLINE CAPSULES WITH INCREASED STABILITY AND METHDS OF PRODUCING THE SAME

BACKGROUND OF THE INVENTION

This application is a continuation of application Ser. No. 757,001, filed July 19, 1985, now abandoned.

1. Field of the Invention

The present invention relates to soft elastic gelatin (SEG) capsules containing oxytetracycline.

2. Description of the Prior Art

SEG capsules have taken on increased significance since most solid and liquid substances can be processed into SEG capsules without difficulties. Oxytetracycline hydrochloride has been processed into SEG capsules in considerable quantities for many years.

The literature describes two crystalline forms of oxytetracycline HCl that are supposed to differ in their hygroscopic properties. Baluteov, V., Farmatsiya (Sofis) 20 (1) 34 (1970); Graskovskays, L.K., Nesterova, L. Ya., Antibiot. (Moakau) 27 (11) 815 (1982). This literature also contains data about the X-ray spectra of both forms A and B. Detailed information about production procedures, conversion behaviors or effects on the pharmaceutical technology, especially on the stability of SEG capsules, are not found in either one of these two papers.

SUMMARY OF THE INVENTION

When producing oxytetracycline HCl containing SEG capsules, the inventors have discovered that depending on the raw materials used, the capsule shells may show embrittlement within a few weeks' time so that even with the slight pressure of a fingernail or during bulk transport, fine cracks may result and the capsules will leak.

Experiments by the inventors proved that there are no differences in the chemical purity of the active substances in the various batches tested since all batches complied with the current pharmacopoeia as far as purity is concerned. However, it was also discovered that oxytetracycline HCl can crystallize into at least three crystalline forms, which differ considerably in their physical properties and their effects on SEG capsules. Of these three crystalline forms, form A is the most stable one in SEG capsules. The crystalline form B can convert to crystalline form A in SEG capsules within a long period of time. The crystalline form C behaves similarly to crsytalline form B. Further investigations showed that half of the oxytetracycline HCl conventionally filled into SEG capsules consists of the crystalline form A and the other half of crystalline form B. Batches of conventional SEG capsules consisting of crystalline form C were not observed.

The three crystalline forms differ in their infrared spectra, X-ray diffraction patterns, hygroscopicity and all other physical properties that result from different crystal structures. While the crystalline form A absorbs less than 1% water in two hours at room temperature and nearly 100% atmospheric moisture, the crystalline form B absorbs more than 8% water under the same conditions.

It was furthermore observed that the crystalline form B absorbs the residual moisture of the capsule shell during the production and storage of SEG capsules, which results in embrittlement of the capsules. The crystalline form A, however, is not able to withdraw moisture from the SEG capsules and, therefore, oxytetracycline HCl containing SEG capsules that include the crystalline form A as an active substance have increased stability. Finally, it was discovered that the crystalline form B after having absorbed a sufficient quantity of water can—in an unpredictable amount of time—convert to crystalline form A, returning the absorbed moisture to the capsule shell. This explains the observation that brittle capsules occasionally lose their embrittlement after a longer period of storage.

Further investigation and characterization of the crystalline forms of oxytetracycline HCl have led the inventors to conclude that the different crystalline forms have a considerable influence on the stability of SEG capsules. Conventional tests have been carried out to measure the increase of the glycerol or sorbitol (softener) content necessary to avoid the embrittlement of the capsule shells of SEG capsules containing the crystalline form B, but these tests were not successful. Surprisingly, it was discovered that the crystalline form B in SEG capsules is not stable and converts in an unforeseeable amount of time to the crystalline form A. This results in a complete softening of the capsule shell such that the capsules get deformed and unsightly and are no longer marketable. In comparison, SEG capsules containing the crystalline form A are stable even after years of storage and can still be commercialized.

Therefore, it is an object of the present invention to provide oxytetracycline HCl SEG capsules having increased stability. Characteristic of such capsules is the fact that the utilized oxytetracycline HCl includes primarily the crystalline form A.

Furthermore, it is an object of the present invention to provide a method of producing oxytetracycline HCl SEG capsules that have increased stability.

Finally, the invention relates to the utilization of the crystalline form A of oxytetracycline HCl for the production of SEG capsules. Oxytetracycline HCl SEG capsules with increased stability are obtained if the oxytetracycline HCl encapsulated includes primarily the crystalline form A.

In principle, it is possible to process mixtures of the crystalline forms A and B, because it can be assumed that small quantities of the crystalline form B together with larger quantities of the crystalline form A do not adversely affect the stability of the capsules to too great an extent. However, during the production of the crystalline forms A and B, only one of the two forms was developed and observed and, therefore, the pure crystalline form A is preferably utilized.

Further objects and embodiments will be made known in the following description of the preferred embodiment and claims.

DESCRIPTION OF THE PREFERRED EMBODIMENTS

SEG capsules are produced according to the methods well known in the art, preferably according to the rotary die procedures for the production of SEG capsules developed and published by R.P. Scherer Corp. All auxiliary and active substances known in the art for use with oxytetracycline HCl can be used in connection with the invention. In all cases the oxytetracycline HCl used should preferably be the crystalline form A. Should the crystalline form A not be available as such, it can be derived from the crystalline forms B or C as follows.

For the production of the form A various possibilities can be taken into consideration. For the sake of simplicity, only those possibilities will be described where oxytetracycline HCl, not the free oxytetracycline base, is used as the starting material and where the production procedure is independent of the crystalline form used.

Oxytetracycline hydrochloride is mixed with 7 times to 10 times the amount of an appropriate solvent in which the oxytetracycline HCl is relatively but not completely insoluble. Under reflux conditions, this suspension is boiled in a rotary evaporator for approximately 1 to 1.5 hours and then heated up to approximately 60° C. Alternatively, the suspension can be stirred for approximately the same length of time at 60° C. in a hermetically sealed container with a magnetic agitator. The hot suspension is then filtered and the crystals are dried under a pressure of 1 mbar at 60° C. Suitable solvents for the recovery of the crystalline form A are, for example, acetone, 1-propanol and 2-propanol. By contrast, the crystalline form B is derived from 0.1 N HCl and the crystalline form C from 96% ethanol by the usual crystalline transformation procedures.

The following examples give further details concerning the crystalline forms A, B and C, as well as their significance to the stability of SEG capsules.

EXAMPLE 1

Figure 1:
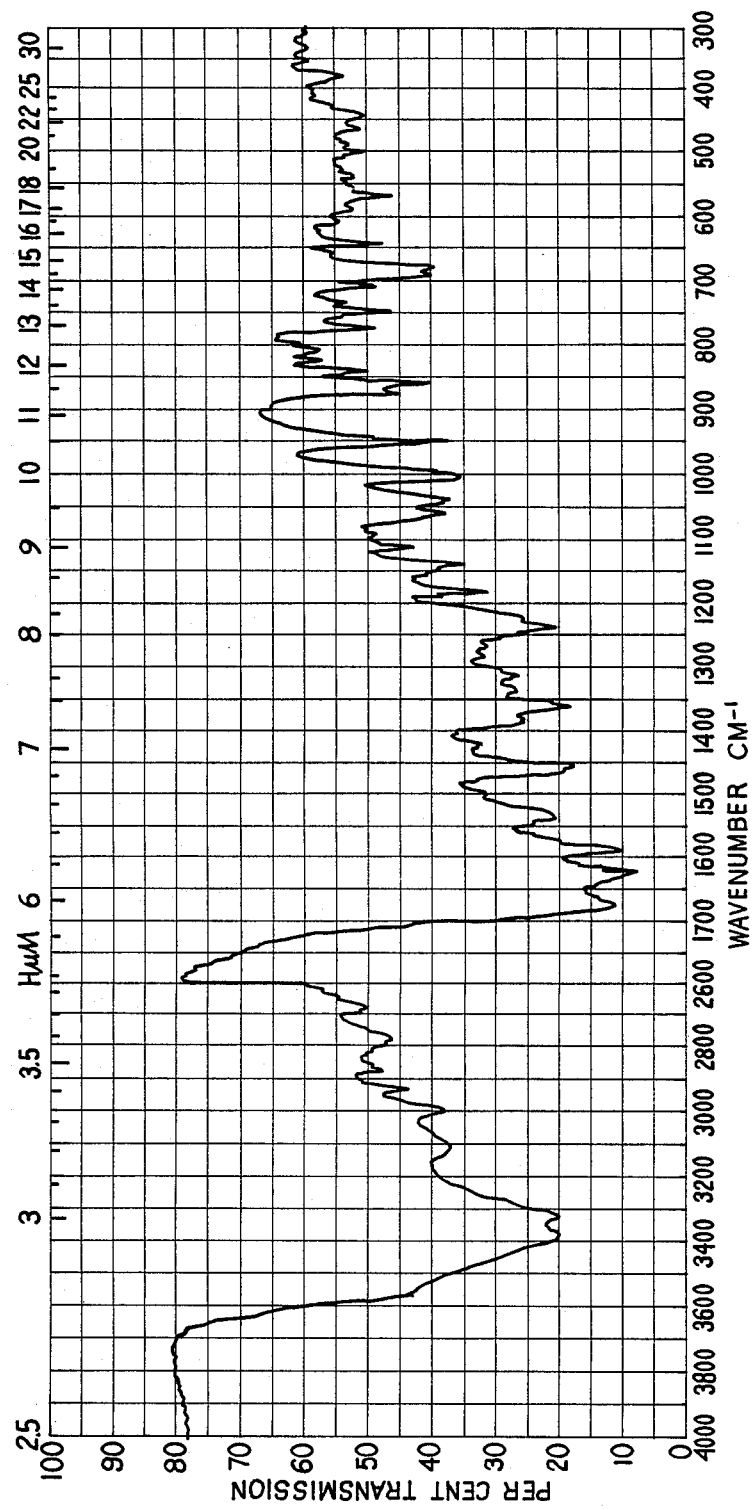
FIG. 1 is an infrared spectrum of the crystalline form A of oxytetracycline hydrochloride.
Figure 2:
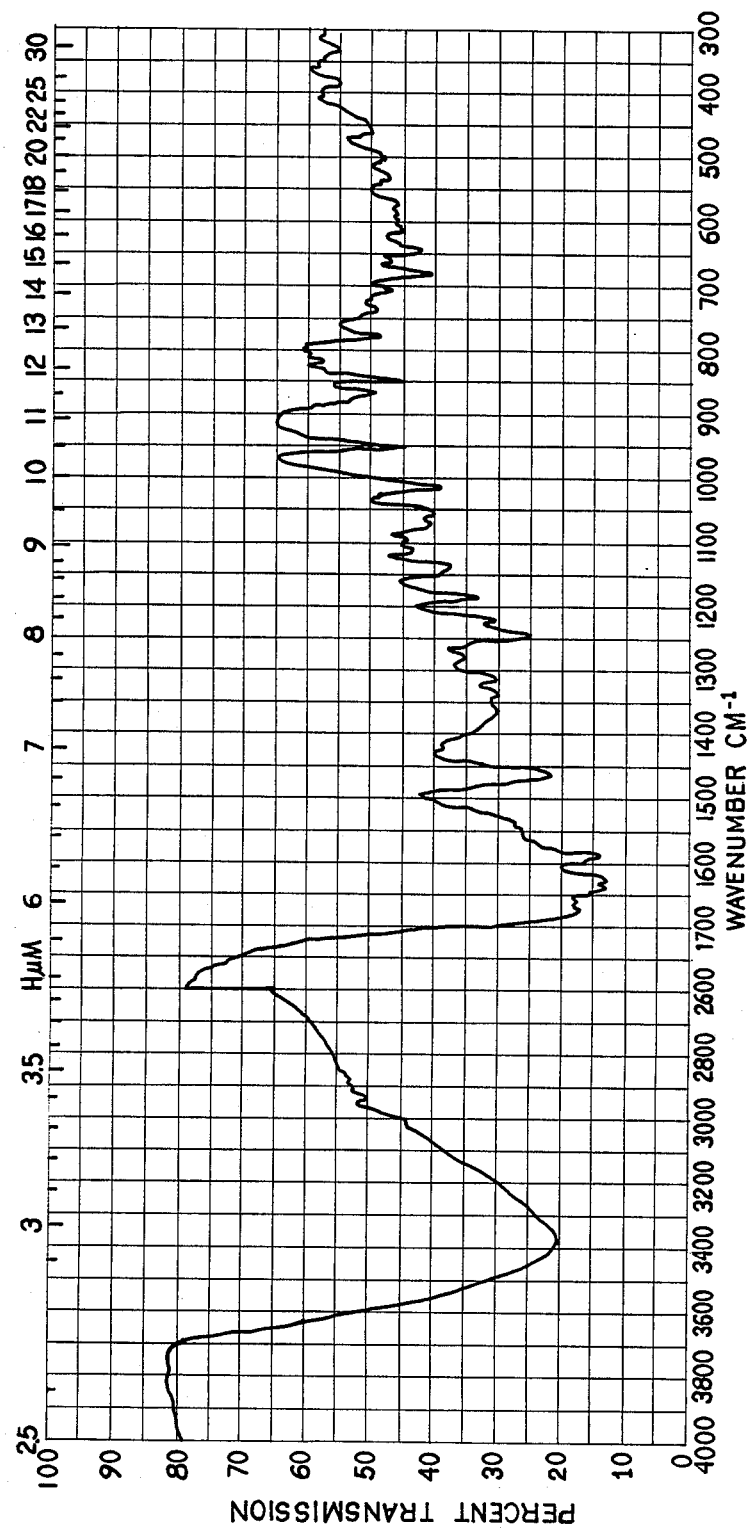
FIG. 2 is an infrared spectrum of the crystalline form B of oxytetracycline hydrochloride.
Figure 3:
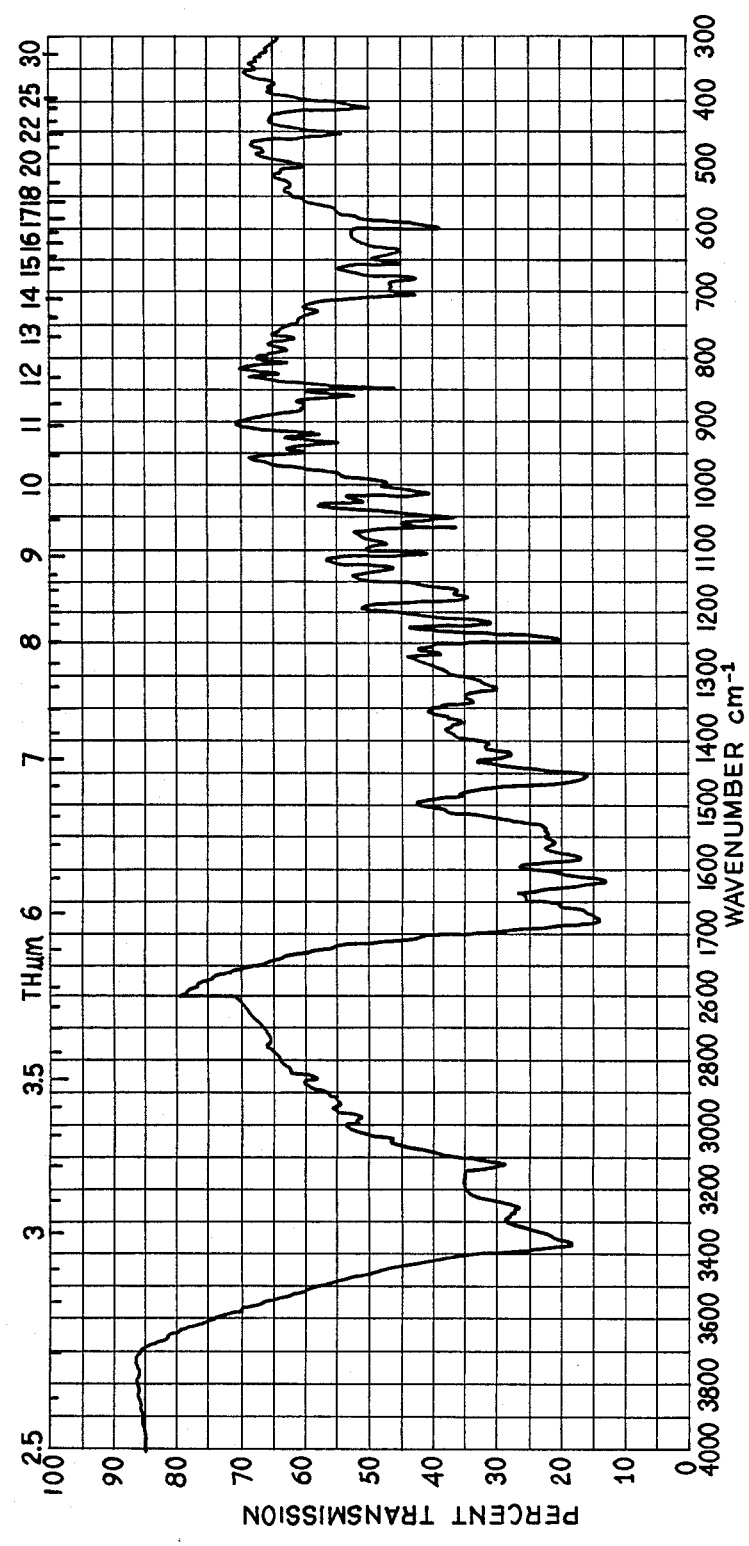
FIG. 3 is an infrared spectrum of the crystalline form C of oxytetracycline hydrochloride.

Samples of the crystalline forms A, B and C were dried at 60° C. and 1 mbar for 48 hours. Their infrared spectra are illustrated in FIGS. 1-3. The infrared spectrum of the crystalline form A is similar to the spectrum known in the literature. "UV-and IR- Spektrum wichtiger pharmaceutischer Wirkstoffe", by Dibbern, Editio Cantor, Aulendorff (1983).

EXAMPLE 2

Figure 4:
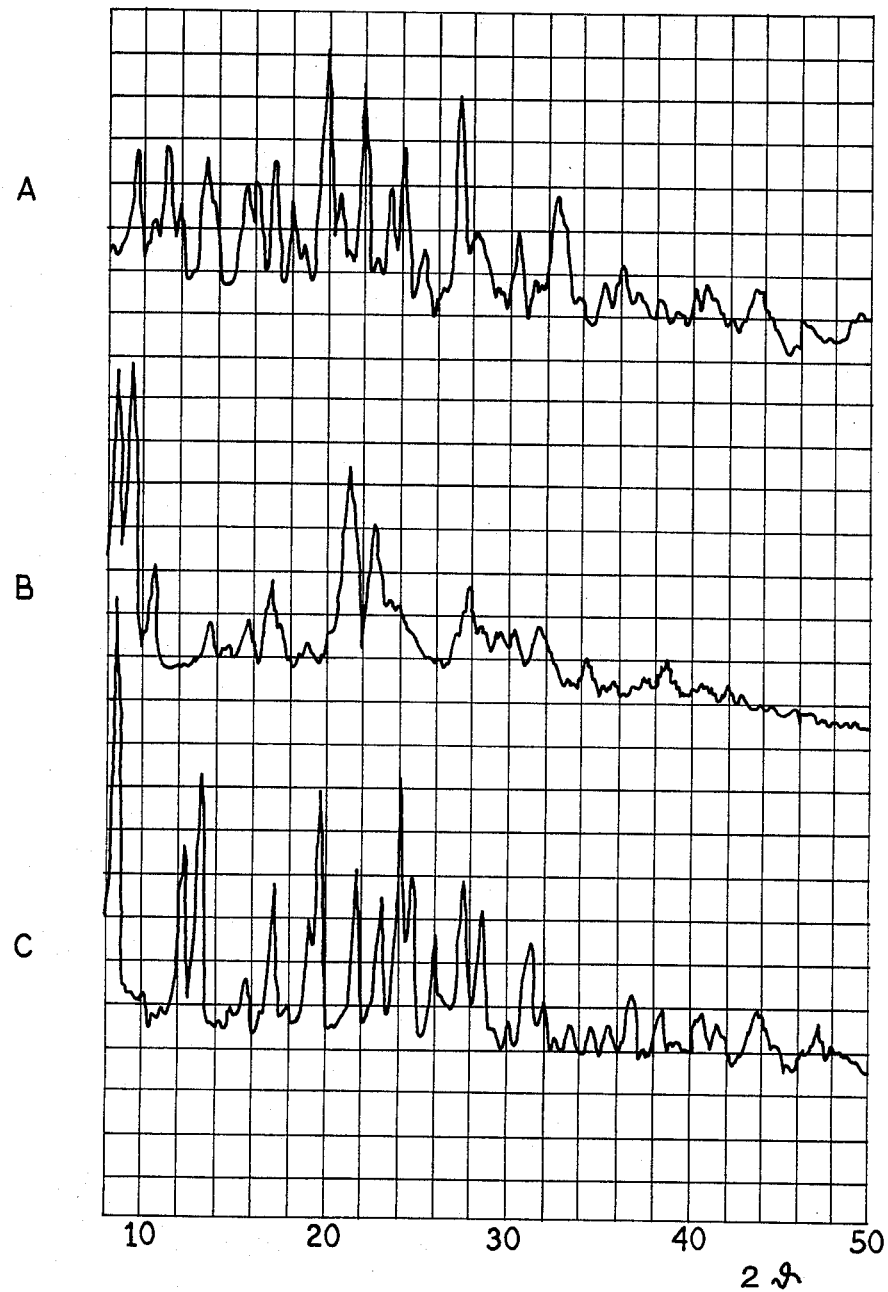
FIG. 4 shows the x-ray diffraction patterns for all three crystalline forms of oxytetracycline hydrochloride.

X-ray diffraction patterns were made of all three crystalline forms by means of Cu, K radiation with counter tube motion of 1 gd/min. The spectra are illustrated in FIG. 4.

EXAMPLE 3

Commercial grade SEG capsules were produced according to the Scherer rotary die procedure. The first batch of capsules contained the crystalline form A of oxytetracycline, the second batch contained form B, and the third batch contained form C. All of these batches of capsules contained an inert fill comprising a neutral triglyceride of fractionated coconut oil fatty acids $C_8$-$C_{10}$ (avaiable from Dynamit Nobel Chemicals under the tradename Miglyol 812), bees wax, hydrogenated vegetable oils and soy lecithin. The capsule shell consisted of 45% gelatin, 22% glycerin (85%), and 33% water and had a volume of 14 minims. Each capsule was filled with 540 mg. of oxytetracycline HCl. The capsules were dried at 20° C. at a relative humidity of 20%.

After drying times of 1, 2, 3, 7, and 9 days, the capsule samples were removed. The IR spectroscopic examination still had not yielded at this point any form alterations of the crystals. The capsules were then stored for 6 months in glass containers, and subsequently the IR spectrum of oxytetracycline HCl was again recorded. Furthermore, the water content of the capsule shell and the water content of the oxytetracycline HCl in the capsule fill was determined. In order to investigate the influence of the temperature on the conversion process, the capsules that had been dried for 9 days were additionally stored at 37° C. and 45° C., and the crystal form was examined via IR spectroscopy after 6 weeks and 3 months. Furthermore, the water content of the capsule shell and the water content of the oxytetracycline HCl fill was measured.

All capsule samples were investigated for brittleness through pressure tests on the capsule seam. With brittle capsules, a distinct cracking of the gelatin shell is observable. This empirical method has often been demonstrated in practice to be more practical than measurements of hardness and bending strength. Additional hardness tests were carried out with the capsules that had been dried for 9 days. The conversion behavior of the crystal forms relative to the storage conditions and the drying time or the moisture content of the capsules is shown in Table I below.

The crystalline form A is fully stable under all conditions. Because of the lack of hydroscopicity in form A, the water content of the oxytetracycline HCl is very low. At no point in time was embrittlement of the capsule shell observed.

By contrast, the crystalline form B was not stable in soft gelatin capsules. The IR spectroscopic examination demonstrated that in capsules dried for only 1 day, form B had transformed into form A after 6 months at room temperature. With capsules dried for a longer period, the form B was still present. With capsules dried for 9 days and for 1 month at 37° C., as well as stored for 6 weeks or 3 months at 45° C., the form B had already changed into form A. This demonstrates that sooner or later all samples change from the form B into form A.

The water content determinations of the capsule shells and of the oxytetracycline HCl fill show that the water content of the crystalline form B of oxytetracycline HCl is high, being approximately 3% in comparison with forms A and C, while the water content in the capsule shells is relatively low. However, as soon as the hygroscopic form B converts to the non-hygroscopic form A, the water content of the oxytetracycline HCl distinctly diminishes. The water content of the capsule shell increases at the same time, since the water is absorbed out of the fill into the shell as a result of the hygroscopicity of the plasticizer glycerin.

The brittleness tests demonstrated that all of the capsules containing form B were only somewhat brittle directly after production. The embrittlement of the capsule shells increased with increasing storage time. After 6 months of storage, all the capsule samples in which the form B was still present were very brittle, while in the samples in which form B had changed into form A, no further brittleness was observed. In agreement with the brittleness tests, the hardness measurements showed a definite increase of the capsule hardness during the 6 months of storage. Because the oxytetracycline HCl is dispersed in the oil based fill, the oxytetracycline is in moisture equilibrium with the capsule shell. The SEG shell is hygroscopic relative to form A and less hygroscopic relative to form B.

With the capsules containing the crystalline form C, no change of the crystal forms was observed with IR spectroscopic examination. The water content of the oxytetracycline HCl was practically the same as with form A with capsules dried for different lengths of time.

The investigations of the brittleness surprisingly showed that the capsules containing form C, directly after production and drying, became clearly brittle, and the brittleness of the capsules during the storage decreased, in agreement with the measured hardness values. After 6 months, the capsules were no longer brittle. The causes for this behavior are not known. The weakening of the capsules is possibly due to the transference of ethanol from the form C to the capsule shell.

TABLE I

| Drying time | Storage Time and Temperature | Change in the crystallization | H₂O content of capsule shell (%) | H₂O content in fill (%) |
|---|---|---|---|---|
| Crystal form A: | | | | |
| 1 day | 6 months, RT | — | 9.9 | 0.9 |
| 2 days | 6 months, RT | — | 9.1 | 0.7 |
| 5 days | 6 months, RT | — | 8.4 | 0.6 |
| 7 days | 6 months, RT | — | 7.5 | 0.5 |
| 9 days | 6 months, RT | — | 6.9 | 0.5 |
| 9 days | 6 weeks, 37° C. | — | 6.5 | 0.6 |
| 9 days | 3 months, 37° C. | — | 6.2 | 0.6 |
| 9 days | 6 weeks, 45° C. | — | 5.8 | 0.5 |
| 9 days | 3 months, 45° C. | — | 5.8 | 0.6 |
| Crystal form B: | | | | |
| 1 day | 6 months, RT | A | 9.9 | 1.0 |
| 2 days | 6 months, RT | — | 7.2 | 5.3 |
| 5 days | 6 months, RT | — | 6.8 | 5.3 |
| 7 days | 6 months, RT | — | 6.2 | 5.2 |
| 9 days | 6 months, RT | — | 5.6 | 4.9 |
| 9 days | 6 weeks, 37° C. | — | 6.0 | 4.9 |
| 9 days | 3 months, 37° C. | A | 9.7 | 1.1 |
| 9 days | 6 weeks, 45° C. | A | 8.6 | 0.9 |
| 9 days | 3 months, 45° C. | A | 9.8 | 1.1 |
| Crystal form C: | | | | |
| 1 day | 6 months, RT | — | 11.4 | 0.7 |
| 2 days | 6 months, RT | — | 9.1 | 0.6 |
| 5 days | 6 months, RT | — | 9.0 | 0.6 |
| 7 days | 6 months, RT | — | 7.5 | 0.7 |
| 9 days | 6 months, RT | — | 7.2 | 0.7 |
| 9 days | 6 weeks, 37° C. | — | 7.5 | 0.8 |
| 9 days | 3 months, 37° C. | — | 6.8 | 0.7 |
| 9 days | 6 weeks, 45° C. | — | 7.0 | 0.8 |
| 9 days | 3 months, 45° C. | — | 6.7 | 0.9 |

EXAMPLE 4

Samples of the crystalline forms A, B and C were inspected with regard to their water content by Karl-Fischer titration before storage and 2 hours after storage at almost 100% relative humidity at room temperature. Table II below shows the result:

TABLE II

| | Water Content (%) before storage | Water Content (%) after 2 hours | Water Absorption (%) |
|---|---|---|---|
| Crystalline Form A | 0.7 | 1.4 | 0.7 |
| Crystalline Form B | 1.2 | 9.7 | 8.5 |
| Crystalline Form C | 1.9 | 8.5 | 6.6 |

The foregoing invention has been described in terms of certain preferred embodiments. However, other embodiments may fall within the spirit and scope of the present invention.

We hereby claim as our invention:

1. A method of producing a soft elastic gelatin capsule containing a selected amount of oxytetracycline hydrochloride comprising the following steps in combination: (1) determining that the selected amount of oxytetracycline hydrochloride comprises at least a majority of the crystalline form A of oxytetracycline hydrochloride; (2) preparing a fill material comprising the selected amount of oxytetracycline hydrochloride; and (3) substantially encapsulating the fill material within a soft elastic gelatin shell, the resulting capsule exhibiting enhanced stability.

2. The method of claim 1 wherein it is determined that the selected amount of oxytetracycline hydrochloride consists essentially of the crystalline form A of oxytetracycline hydrochloride.

3. The method of claim 1 wherein it is determined that the selected amount of oxytetracycline hydrochloride consists of the crystalline form A of oxytetracycline hydrochloride.

4. The method of claim 1 wherein the selected amount of oxytetracycline hydrochloride is determined to compromise at least a majority of the crystalline form A of oxytetracycline hydrochloride by infrared spectroscopy or X-ray spectroscopy of the selected amount.

5. The method of claim 1 wherein the selected amount of oxytetracycline hydrochloride is determined to comprise at least a majority of the cyrstalline form A of oxytetracycline hydrochloride by measuring the hygroscopicity of the selected amount.

6. The method of claim 1 wherein the selected amount of oxytetracycline hydrochloride is determined to comprise at least a majority of the crystalline form A of oxytetracycline hydrochloride by preparing the selected amount according to a method known to result in the formation of the crystalline form A of oxytetracycline hydrochloride.

* * * * *